United States Patent
Pazart et al.

(10) Patent No.: US 9,770,557 B2
(45) Date of Patent: Sep. 26, 2017

(54) SECURE PERFUSION SYSTEM

(75) Inventors: Lionel Pazart, Besançon (FR); Bruno François Marcel Wacogne, Traitiefontaine (FR); Christian Gérard Daniel Pieralli, Besançon (FR); Wilfrid Hervé Boireau, Mondon (FR); Pascal Charles Serge Morel, Besançon (FR)

(73) Assignees: Centre National de la Recherche Scientifique, Paris (FR); Centre Hospitalier Universitaire De Besancon, Besancon (FR); Universite De Franche Comte, Besancon (FR); Etablissement Francais Du Sang, La Paine Saint Denis (FR)

(*) Notice: Subject to any disclaimer, the term of this patent is extended or adjusted under 35 U.S.C. 154(b) by 760 days.

(21) Appl. No.: 13/508,179
(22) PCT Filed: Oct. 29, 2010
(86) PCT No.: PCT/FR2010/000714
§ 371 (c)(1),
(2), (4) Date: Nov. 16, 2012
(87) PCT Pub. No.: WO2011/055031
PCT Pub. Date: May 12, 2011

(65) Prior Publication Data
US 2013/0060228 A1 Mar. 7, 2013

(30) Foreign Application Priority Data
Nov. 5, 2009 (FR) .................................. 09 05329

(51) Int. Cl.
*A61M 5/172* (2006.01)
*A61B 5/153* (2006.01)
(Continued)

(52) U.S. Cl.
CPC ....... *A61M 5/1723* (2013.01); *A61B 5/15003* (2013.01); *A61B 5/153* (2013.01);
(Continued)

(58) Field of Classification Search
CPC .......... G01N 2333/195; G01N 33/6803; G06F 19/18; G06F 19/24; Y10S 128/925;
(Continued)

(56) References Cited

U.S. PATENT DOCUMENTS

| 4,573,968 A | 3/1986 | Parker |
| 4,900,321 A | 2/1990 | Kaufman et al. |
| 2011/0183310 A1* | 7/2011 | Kravitz et al. ................. 435/1.2 |

FOREIGN PATENT DOCUMENTS

| WO | WO 99/56630 A1 | 11/1999 |
| WO | WO 2006/088771 A2 | 8/2006 |
| WO | WO 2007/033025 A2 | 3/2007 |

OTHER PUBLICATIONS

International Search Report and Written Opinion for Application No. PCT/FR2010/000714 dated Jan. 7, 2011.

* cited by examiner

*Primary Examiner* — Imani Hayman
(74) *Attorney, Agent, or Firm* — Alston & Bird LLP

(57) ABSTRACT

The invention relates to a secure system for the perfusion of a body liquid, enabling a final control of compatibility of a treatment with the patient and/or the medical situation previously diagnosed by a doctor, in a simple, efficient and energy-saving manner. To this end, the system includes a fluidic circuit of a perfusion having a perfusion catheter, a perfusion tubing and a container for the determined perfusion product to be perfused to a patient. The system is also configured to take a body liquid sample from a patient and to analyze and compare the body liquid sample to the determined perfusion product so as to control the flow of the perfusion product.

23 Claims, 8 Drawing Sheets

(51) Int. Cl.
*A61B 5/155* (2006.01)
*A61B 5/157* (2006.01)
*A61B 5/00* (2006.01)
*A61M 5/168* (2006.01)
*A61B 5/15* (2006.01)
A61B 5/145 (2006.01)
A61M 1/02 (2006.01)
A61M 5/14 (2006.01)

(52) U.S. Cl.
CPC .............. *A61B 5/155* (2013.01); *A61B 5/157* (2013.01); *A61B 5/150221* (2013.01); *A61B 5/150992* (2013.01); *A61B 5/4839* (2013.01); *A61B 5/6866* (2013.01); *A61M 5/16877* (2013.01); *A61B 5/14503* (2013.01); *A61M 1/02* (2013.01); *A61M 5/1407* (2013.01); *A61M 2205/3303* (2013.01); *A61M 2205/609* (2013.01)

(58) Field of Classification Search
CPC ... A61B 5/1427; A61B 5/14503; A61B 5/153; A61B 5/155; A61B 5/157; A61B 5/4839; A61B 5/6866; A61M 1/02; A61M 2205/3303; A61M 2205/609; A61M 5/1407; A61M 5/16877; A61M 5/1723
See application file for complete search history.

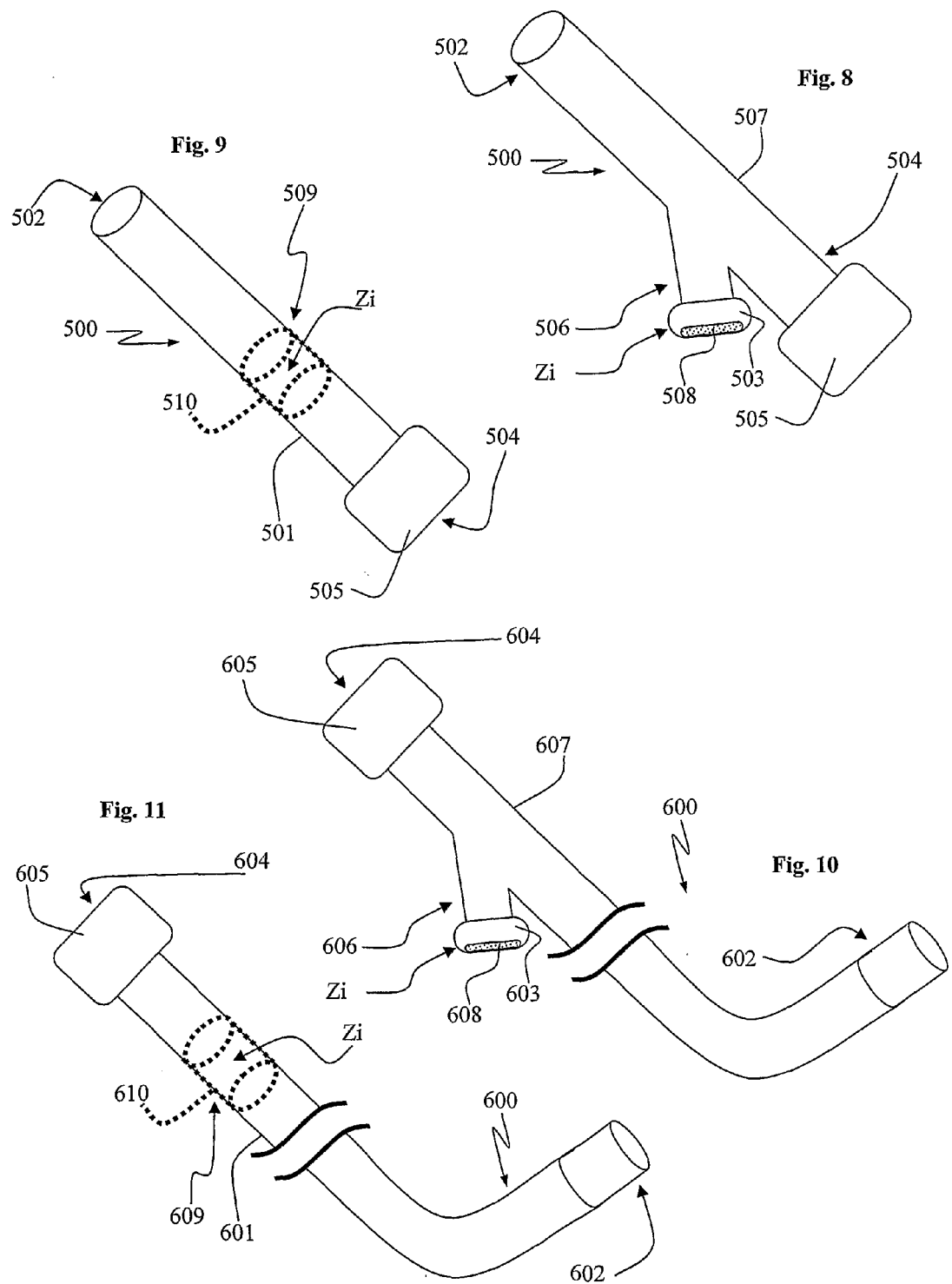

SECURE PERFUSION SYSTEM

FIELD OF THE INVENTION

The invention relates to a system for secure perfusion, in particular for blood transfusion, and to an implementation process.

BACKGROUND OF THE INVENTION

After the doctor has diagnosed a given medical situation (illness, accident, hemorrhage, etc.), it may be necessary to treat it by administering to the patient a suitable product: a medicament, blood, etc. The invention relates to an administration via injection, in particular via a perfusion.

As is known, perfusion into a peripheral vein is set up in the following manner.

After having located a peripheral vein, the patient's skin is pierced using a needle covered with a catheter (such a device is known under the brand Cathlon®). Once the needle is positioned in a vein, the distal end of the catheter is pushed into the vein, the needle is removed, and the proximal end of the catheter is fastened to the patient's skin using a sterile dressing. Various diameters of catheter exist, and are generally expressed in terms of gauge (G). The diameter of the catheter used depends on the condition of the patient, on the operation to be carried out (sample collection or injection) and on the age of the patient. For example, the following catheters will be chosen: 22 to 24 gauge for newborns, 22 gauge for children from 1 month to 3 years old, 20 gauge for older children. For adults, it will be possible to choose catheters from 18 gauge (i.e. an external diameter of 1.1 mm to 1.3 mm) up to 14 gauge (i.e. an external diameter of 1.8 to 2.2 mm).

A table showing the connection between the "gauge" unit and the metric system is given below:

| gauge (internal diameter of the needle) | External diameter (mm) |
| --- | --- |
| 24 G | 0.6 to 0.7 |
| 22 G | 0.7 to 0.9 |
| 20 G | 0.9 to 1.1 |
| 18 G | 1.1 to 1.3 |
| 16 G | 1.5 to 1.8 |
| 14 G | 1.8 to 2.2 |

The catheter bears, at its proximal end, a connection device, for example of Luer lock type, and at its distal end perfusion tubing. This connection device may be such that when the catheter is not connected, its proximal end is closed and the blood cannot escape.

In general, after connecting the catheter, a safety loop is produced with the tubing that is fastened to the patient's skin with tape. This safety loop prevents the catheter from being immediately pulled out in case of tension on the perfusion tubing.

The proximal end of the tubing is in fluid communication with an expansion vessel connected to a rigid or flexible bag of perfusion product attached to a pole. The latter must be high enough relative to the patient's catheter so that the perfusion product flows by simple gravity toward the catheter then the vascular system of the patient.

The tubing comprises, preferably, a toothed wheel for controlling the flow rate of perfusion, or other control system.

Before letting the product flow via perfusion, it is essential to carry out a final compatibility check between the treatment previously prescribed by the doctor and the treatment that is about to be given to the patient. This check makes it possible to verify that the product indeed corresponds to the diagnosed medical situation and/or that it will be well tolerated by the patient.

For example, for blood transfusion, when a doctor has prescribed a transfusion for a patient of given blood group, the nurse must ensure that the blood bags that he/she has are compatible with the patient's blood group since there can be errors in allocating blood bags or in the identification of the patient or of the blood bags.

Conventionally, the nurse uses card stock impregnated with anti-A and anti-B reagent on which he/she deposits blood from the patient (obtained by pricking the end of the finger or a vein) and blood from a sample from the transfusion bag. For this purpose, the transfusion bags have a main container for the transfusion, and secondary sampling containers, that can be separated from the main container.

The nurse then assesses the presence of agglutinates on the card stock and compares the reactions obtained with the patient's blood and with the blood from the sample. The nurse must then apply the compatibility rules that he/she has learnt in order to interpret the results of the test. This interpretation may be tricky, especially in the presence of weak antigens or in certain pathologies.

Thus, it has been noticed that there are still many errors due to fatigue, due to an emergency situation or to inattention, during the interpretation of these tests, but also during the setting up of the transfusion bag and, more generally, of the second perfusion.

In particular, it has been noticed that only too often the product of the second perfusion is not that which had been prescribed by the doctor.

These errors may simply slow down the patient's recovery, for example when the dosage of the perfused product is lower than that which is prescribed by the doctor in order to cure the patient. They may also lead to the death of the patient, for example when the blood transfused is incompatible with the patient's blood group (A, B, AB or O), or when the patient is allergic to the antibiotic perfused whereas the patient was not allergic to the antibiotic initially prescribed.

Handling errors may also occur that are dangerous for the nursing staff if there is direct exposure to the patient's blood.

To overcome this problem, the current solutions aim to ensure that the information written on the transfusion bag and information written on a support borne by the patient agree. These technologies mainly consist of bar code or RFID chip control systems. However, handling errors still exist, especially due to perfusion bag labeling errors or patient identification errors.

SUMMARY OF THE INVENTION

A first objective of the present invention is therefore to propose a perfusion system that makes it possible to carry out, simply, effectively and energy efficiently, a final compatibility check of a treatment, previously chosen by a doctor, with the patient and/or the medical situation previously diagnosed by a doctor.

For this, the invention proposes to produce a perfusion system comprising a final check on the same perfusion line connected to the patient.

Furthermore, when a (human or animal) patient is perfused, for example with a therapeutic product (saline solution, antibiotic solution, etc.), it may be necessary to give the patient a second perfusion of another product, such as blood, after the doctor has diagnosed a given medical situation (illness, accident, hemorrhage, etc.). In the example described, it is a need for blood.

In this case, an authorized person (doctor, nurse or veterinarian) must set up a second perfusion line, specific for the transfusion of blood.

Conventionally, for a peripheral venous route, the second perfusion is set up on the controlateral arm. The patient is therefore subjected to a first needle insertion for fitting the first perfusion, then a second needle insertion for fitting the second perfusion.

Within the context of the present invention, a sample of body fluid is collected in order to carry out a final check before injecting the product of the second perfusion. The patient will therefore have to undergo a third needle insertion for the sample collection.

Another possibility consists in placing tubing equipped with a three-way stopcock in order to connect thereto the tubing of the second perfusion without it being necessary to insert a needle again into the patient. Then, in this example, the patient will have to undergo a second needle insertion for the sample collection.

In order to avoid a second needle insertion into an already perfused patient, document WO 2006/088771 proposes to equip a conventional perfusion with a reversible pump associated with control means. The latter is designed to intermittently interrupt the operation of the perfusion pump in the forward direction (that is to say from the bag of perfusion product toward the patient), in order to operate the pump in the rearward direction (that is to say from the patient to a sample collection circuit). In this way, it is possible to collect a sample of the patient's blood via the perfusion catheter.

However, this device requires meticulous control of the pump and a complex fluid circuit comprising multiple valves.

Moreover, this system may be noisy (due to the operation of the pump) and requires a source of energy for the collection of a sample of blood and the injection of the perfusion product.

Another objective of the invention is therefore to propose a simple, effective and energy-efficient device, that makes it possible to easily collect a sample of body fluid while avoiding another intrusion into the body of the patient, and while limiting the need for a purge prior to the sample collection.

The positioning of the perfusion catheter in the body of the patient is not part of the present invention. On the contrary, the invention makes it possible to take advantage of a perfusion already set up in a patient in order to collect a sample of body fluid, such as blood, and avoid another needle insertion into the body of the patient.

For this purpose, one subject of the invention is a system for the secure perfusion of a body fluid, comprising:
 a fluid circuit of a perfusion comprising a perfusion catheter, perfusion tubing and a container of given perfusion product to be perfused to a patient;
 a means for collecting a sample of a body fluid from a patient;
 a sample collection container equipped with a means of fluid connection with the sample collection means;
 a means of analyzing and comparing the collected body fluid and a sample of given product;
 a means of fluid connection between the analysis means and the sample collection container;
 a means for controlling the flow of the perfusion product in the tubing, the analysis and comparison means being capable of transmitting to the flow control means, a comparison information of the collected body fluid and the sample of given product.

According to other embodiments:
the analysis means may be capable of controlling the flow control means so that it blocks the flow of the perfusion product if the comparison information indicates that the body fluid and the perfusion product are incompatible, and so that it permits the flow of the perfusion product if the comparison information indicates that the body fluid and the perfusion product are compatible;
the secure perfusion system may comprise a means for displaying the comparison information of the collected body fluid and the sample of given product;
the analysis means may be capable of controlling the flow control means so that it automatically generates the flow of the perfusion product if the body fluid and the perfusion product are compatible, and so that it does not generate the flow of the perfusion product if the body fluid and the perfusion product are incompatible;
the analysis means may comprise a reaction chamber and a detection means;
the sample collection means may comprise:
 a sample collection channel comprising a proximal end intended to be connected to the sample collection container, and a distal end, and
 a sample collection device intended to be incorporated into the fluid circuit of a perfusion, and comprising a tubular structure for connection to the fluid circuit of the perfusion, equipped:
  with a zone of intubation, in use, of a sample collection channel comprising a distal end; and
  with a means for holding, in use, in the tubular structure, the portion of the sample collection channel comprising a distal end, so that, in use, said distal end is pointed toward the perfusion catheter, in the flow direction of the perfusion product, from a container of perfusion product to the perfusion catheter;
the intubation zone may be arranged so that, in use, it is positioned at a given maximum vertical distance from the proximal end of the catheter;
the given maximum vertical distance may be between 0 cm and 50 cm;
the portion comprising the distal end of the sample collection channel may be fixed in the tubular structure, and a portion comprising a proximal end of the sample collection channel emerges outside of the tubular structure level with the intubation zone;
the intubation zone may comprise an insertion means suitable for enabling, in use, the insertion, into the tubular structure, of the portion of the sample collection channel comprising the distal end;
the insertion means may be chosen from:
 a membrane made of a leaktight material that retains its leaktightness after having been pierced; and
 a leaktight connector;
the leaktight material that retains its leaktightness after having been pierced may be chosen from a silicone polymer, such as polydimethylsiloxane (PDMS), polymethyl methacrylate (PMMA), polyvinyl chloride (PVC) and Tygon®;
the sample collection device additionally may comprise:
 a means of connection to a proximal end of the perfusion catheter, and a means of connection to a distal end of the perfusion tubing;

the sample collection channel may have a length between its two ends of between 10 cm and 100 cm, preferably between 20 cm and 50 cm;

the secure perfusion system may comprise a perfusion catheter comprising:
  a distal end intended to be inserted into a patient;
  a proximal end intended to be connected with a distal end of the perfusion tubing;
  the sample collection device arranged between the distal end and the proximal end, and comprising a tubular structure for connection to the fluid circuit of the perfusion, equipped:
    with a zone of intubation, in use, of a sample collection channel comprising a distal end; and
    with a means for holding, in use, in the tubular structure, the portion of the sample collection channel comprising a distal end, so that, in use, said distal end is pointed toward the perfusion catheter, in the flow direction of the perfusion product, from a container of perfusion product to the perfusion catheter;

the secure perfusion system may comprise perfusion tubing comprising:
  a proximal end intended to be connected to a container of a perfusion product;
  a distal end intended to be connected with a proximal end of a perfusion catheter inserted into a patient;
  the sample collection device arranged between the distal end and the proximal end, and comprising a tubular structure for connection to the fluid circuit of the perfusion, equipped:
    with a zone of intubation, in use, of a sample collection channel comprising a distal end; and
    with a means for holding, in use, in the tubular structure, the portion of the sample collection channel comprising a distal end, so that, in use, said distal end is pointed toward the perfusion catheter, in the flow direction of the perfusion product, from a container of perfusion product to the perfusion catheter;

the intubation zone may be positioned at a given maximum vertical distance from the proximal end of the catheter; and/or the given maximum vertical distance may be between 0 cm and 50 cm.

The invention also relates to a process for implementing a preceding secure perfusion system, the sample collection means of which has been previously fitted to a patient, comprising the following steps:
  placing the sample collection means, the sample collection container and the analysis and comparison means in fluid communication;
  bringing the sample collection container to a height below that of the catheter of the patient, so that the body fluid flows into the sample collection channel, toward the sample collection container;
  holding the sample collection container at a height below that of the catheter of the patient for a sufficient time to obtain, in the sample collection container, a volume sufficient to constitute a collection of a sample of body fluid;
  analyzing and comparing the collected body fluid and the sample of given product;
  generating comparison information of the collected body fluid and the sample of given product;
  transmitting the comparison information to a means for controlling the flow of the perfusion product;
  blocking the flow of the perfusion product if the comparison information indicates that the body fluid and the perfusion product are incompatible, and permitting the flow of the perfusion product if the comparison information indicates that the body fluid and the perfusion product are compatible.

According to other embodiments:

the process may comprise, in addition, a step of displaying the comparison information of the collected body fluid and the sample of given product;

the process may comprise the following steps:
  incorporating the sample collection device into a fluid circuit of a first perfusion previously fitted to a patient equipped with a perfusion catheter, in an outer portion of the fluid circuit relative to the body of the patient;
  holding, inside the tubular structure, the portion of the sample collection channel comprising the distal end, so that said distal end is pointed toward the perfusion catheter, in the flow direction of the perfusion product, from a container of perfusion product to the perfusion catheter;
  placing the sample collection channel, the sample collection container and the analysis and comparison means in fluid communication;
  bringing the sample collection container to a height below that of the catheter of the patient, so that the body fluid flows into the sample collection channel, countercurrent compared to the perfusion product, then toward the sample collection container;
  holding the sample collection container at a height below that of the catheter of the patient for a sufficient time to obtain, in the sample collection container, a volume sufficient to constitute a collection of a sample of body fluid;
  analyzing and comparing the collected body fluid and a sample of given product;
  generating comparison information of the collected body fluid and the sample of given product;
  transmitting the comparison information to a means for controlling the flow of the product of a second perfusion;
  blocking the flow of the product of the second perfusion if the comparison information indicates that the body fluid and the product of the second perfusion are incompatible, and permitting the flow of the product of the second perfusion if the comparison information indicates that the body fluid and the product of the second perfusion are compatible;

the sample collection device may be arranged so that, in use, the intubation zone is positioned at a given maximum vertical distance from the proximal end of the catheter;

the given maximum vertical distance may be between 0 cm and 50 cm; and/or the distal end of the sample collection channel may be arranged at a given distance from a proximal end of the perfusion catheter, said distance being referred to as the "butt-joining distance" and being between 0 cm and 20 cm, preferably between 0 cm and 3 cm.

BRIEF DESCRIPTION OF THE DRAWINGS

Other features of the invention will be set out in the detailed description below, made with reference to the appended figures that represent, respectively:

FIG. 4*a*, a partial enlargement of FIG. 4 illustrating, in detail, the sample collection device according to the invention;

FIG. 5*a*, a partial enlargement of FIG. 5 illustrating, in detail, the sample collection device according to the invention;

FIG. 6*a*, a partial enlargement of FIG. 3 illustrating, in detail, the sample collection device according to the invention;

FIGS. 8 and 9, schematic plan views of two embodiments of a perfusion catheter according to the invention;

FIGS. 10 and 11, schematic plan views of two embodiments of perfusion tubing according to the invention;

DETAILED DESCRIPTION OF THE INVENTION

Figure 1:
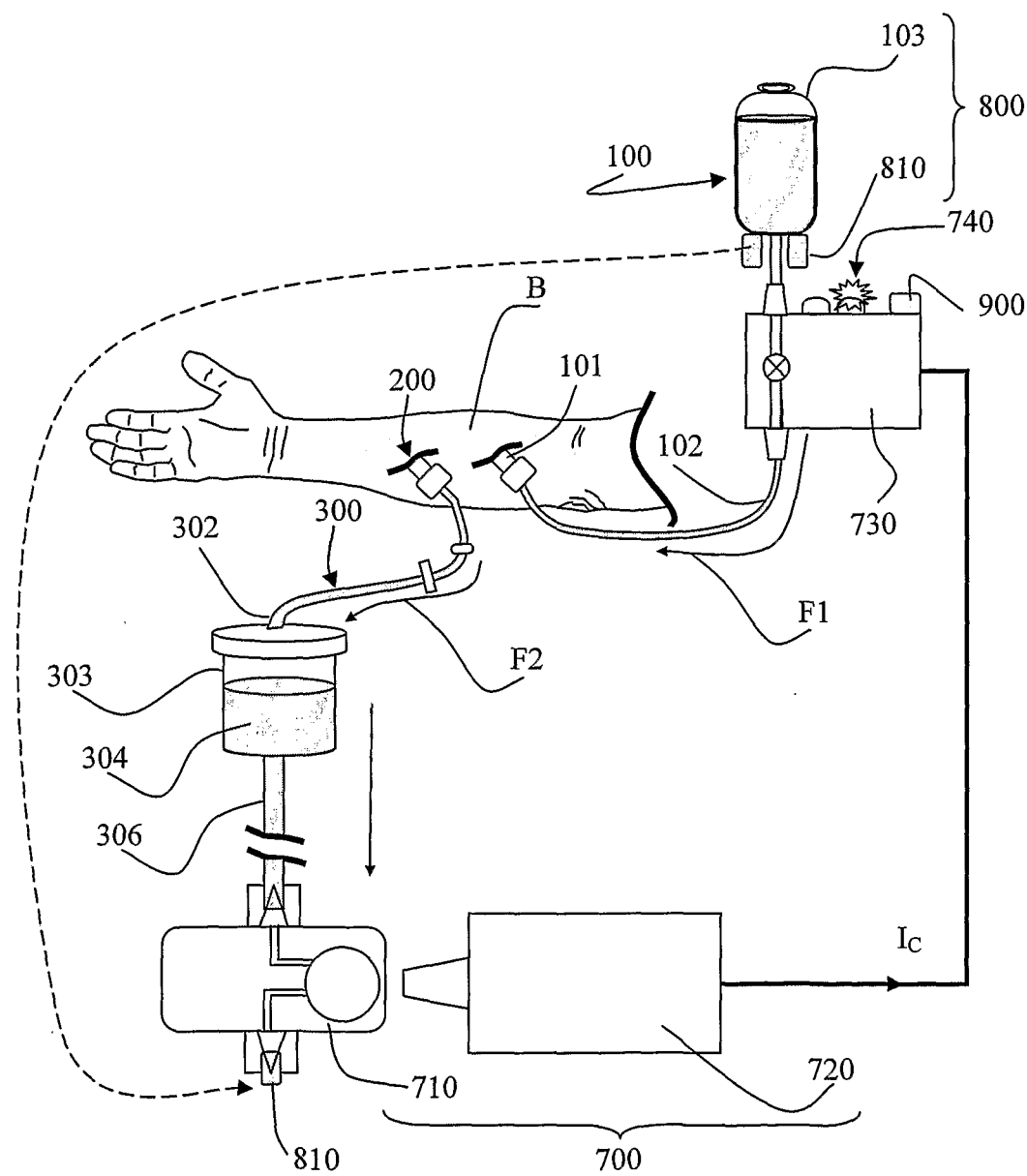
FIG. 1, a schematic plan view of a first embodiment of a secure perfusion system according to the invention.

The example described subsequently relates to secure blood transfusion. However, the invention covers any perfusion product that has to be administered to a patient after a test of compatibility with the patient or the illness from which the patient suffers (urine, cerebrospinal fluid, pleural fluid, ascites fluid, peritoneal fluid, etc.).

The secure perfusion system according to the invention may advantageously be used to carry out a secure blood transfusion.

This system and the implementation thereof are illustrated in FIGS. 1 to 6*a* described below.

The secure perfusion system according to the invention generally comprises a fluid circuit of a first perfusion 100 comprising a perfusion catheter 101, perfusion tubing 102 and a container 103 of given perfusion product to be administered to a patient B. A means 730 for controlling the flow of the perfusion product in the tubing is associated with this circuit in order to permit or prohibit the flow of the product.

The positioning of the perfusion catheter in the body of the patient is not part of the present invention.

Figure 2:
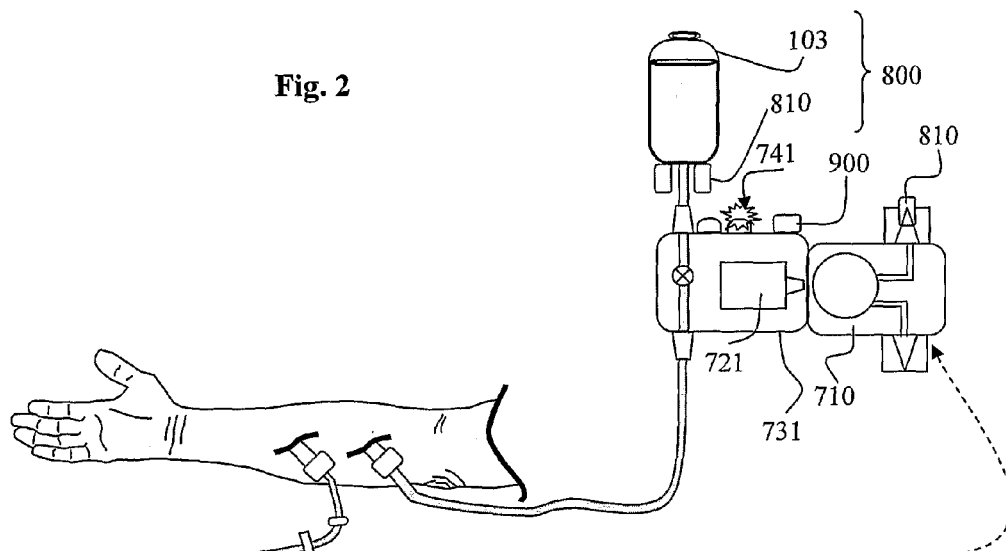
FIG. 2, a schematic plan view of a second embodiment of a secure perfusion system according to the invention.
Figure 3:
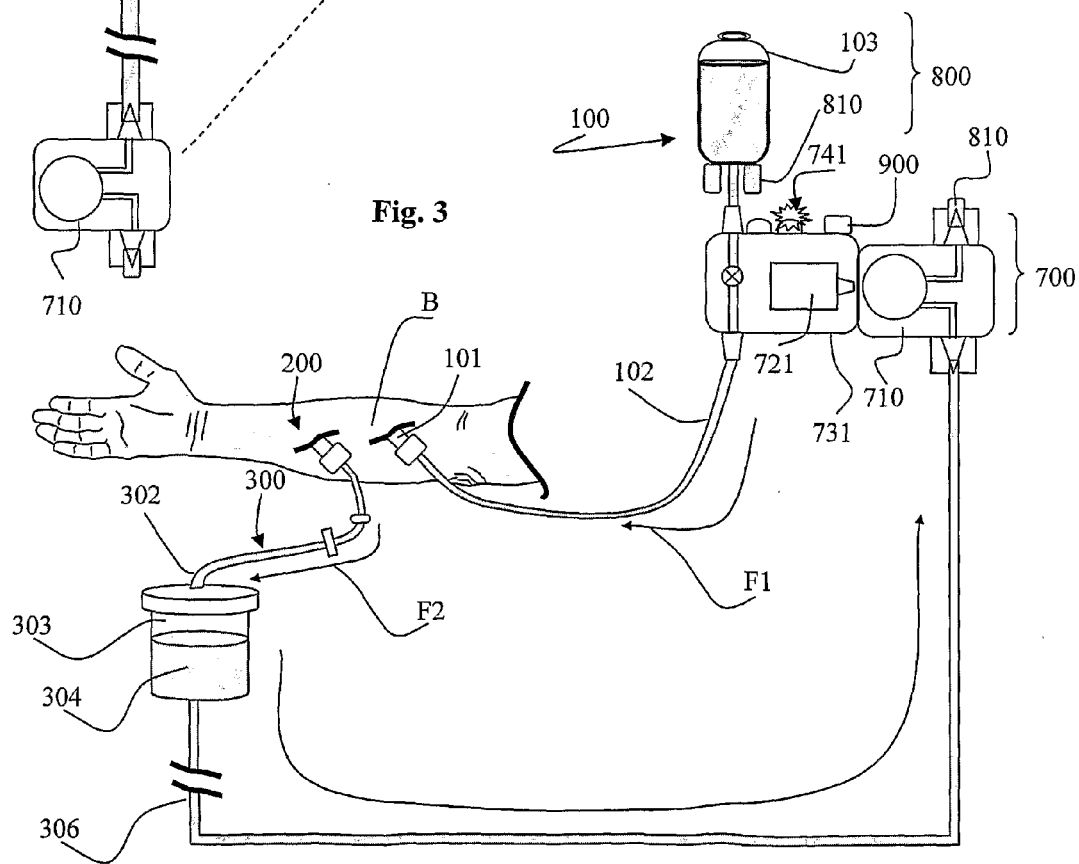
FIG. 3, a schematic plan view of a third embodiment of one particular use of the sample collection device according to the invention.

The secure perfusion system according to the invention also comprises a means 200 for collecting a sample of a body fluid from a patient. In FIGS. 1 to 3, this sample collection means comprises a conventional catheter 201, to be fitted to the patient, preferably in the patient's vascular system. FIGS. 4 to 6*a* present one particular embodiment of a sample collection means 200.

In use, the sample collection means 200 is in fluid connection with a sample collection container 303 by means of a channel 300. In the entire remainder of the present description, the sample collection containers advantageously have a closeable air inlet.

Moreover, by means of a line 306, the sample collection container 303 is in fluid connection with a means 700 for analyzing and comparing the collected body fluid and a sample of given product. In the example described of a secure blood transfusion according to the invention, the given product is blood stored in one of the secondary sampling containers 810, separable from the main container 103 of the transfusion bag 800.

The analysis means 700 is capable of analyzing the collected body fluid and the sample of given product 810, and also of comparing them with one another. The analysis and comparison means 700 is also capable of transmitting, to the flow control means 730, comparison information $I_C$ of the collected body fluid 304 and the sample of given product 810.

The reaction chamber 710 may have any form suitable for the reaction that must be detected.

One exemplary embodiment of a reaction chamber is a cassette comprising a biochip provided with a fluid circuit.

One particularly advantageous example, within the context of a secure blood transfusion system, is the use of biofunctionalized gold biochips 710 in combination with a detection device 720 based on optical transductions (such as those sold by the company GE Healthcare under the name "BIAcore system").

Based on surface plasmon resonance, this type of device measures a variation of the resonance extinction angle (dependant on a variation of refractive index at the gold/dielectric interface) which may be correlated to a variation in mass.

Carried out on a glass support provided with a thin layer of gold, the functionalization takes place in two steps. A first step enables the reconstitution of an organic thin film having certain activatable chemical functions (of the type: SH, COOH, $NH_2$, etc.) for the subsequent grafting of antibodies. During the second step, this layer is activated and the antibodies deposited at its surface are immobilized.

The inventors have discovered that after chemical treatment of the gold surface, the immobilization of the anti-A and anti-B antibodies of IgM type was significantly improved at a pH of around 4.65.

Under these pH conditions, the degree of grafting reaches on average 1500 IgM/$\mu m^2$ which makes it possible to involve up to 100 000 antibodies per red corpuscle captured.

This leads to a strong interaction between the erythrocytes and the immunosensor having a surface functionalized by anti-A and anti-B IgMs, even after several rinses.

Thus, the means 700 is capable of analyzing the collected blood 304 by interpreting the detection information, resulting from the detection means 720, relating to interactions between the corpuscles of the blood and the antibodies present on the biochip.

This interaction is highly sensitive and enables an analysis of blood compatibility even in the case of pathology or of weak antigens.

Other types of interaction and other means of detection than those described previously may be used to analyze the blood (detection of viruses, proteins, circulating rare cells, etc.) or other body fluids collected.

In the embodiment from FIG. 1, the analysis means 700 comprises a reaction chamber 710 and a detection means 720.

The detection means 720 of the analysis means 700, located in the vicinity of the reaction chamber 710, transmits comparison information $I_C$ to a flow control means 730 of the first perfusion. The flow control means 730 is preferably equipped with a means 740 for displaying the comparison information.

Practically, the analysis means 700 is, in this embodiment, located below the catheter of the patient, in the vicinity of the sample collection container 303.

Such an embodiment has the advantage of requiring only a short length of fluid lines (channel 300 and line 306). However, the overall space requirement of the system may be large since it comprises an analysis means 700 and an independent flow control means 730.

In the embodiment illustrated in FIG. 2, the reaction chamber 710 is, as in FIG. 1, connected to the container 303 of collected fluid and to a sample 810 of given product.

When the reaction chamber is ready for the analysis and the comparison, the operator disconnects it from the line 306 (a closure valve, not represented, is preferably provided for this purpose) and connects it to a flow control means 731. The latter is equipped with a detection and analysis means 721 and a means 741 for displaying the comparison information $I_C$ (not represented) transmitted by the means 721. The connection of the chamber 710 to the control means 731 may be made using an attachment means (not represented).

The attachment means may be a clamp sandwiching the reaction chamber 710, so that the position of the chamber is optimal for the detection and analysis by the means 721.

This embodiment has the advantage of being more compact than that illustrated in FIG. 1. However, it requires a step of fluid disconnection of the reaction chamber 710, which may constitute a risk of contact between the operator and the fluid collected.

In the embodiment illustrated in FIG. 3, the sample collection container 303 is in fluid communication, via a line 306, with the reaction chamber 710.

The line 306 is long enough to enable an operator, when the reaction chamber is ready for the analysis and comparison, to place the chamber 710 on a means (not represented) for attachment to a flow control means 731 similar to that described in FIG. 2. This is equipped with a detection and analysis means 721 and with means 741 for displaying the comparison information $I_C$ (not represented) transmitted by the means 721.

The attachment means may be a clamp sandwiching the reaction chamber 710, so that the position of the chamber is optimal for the detection and analysis via the means 721.

This embodiment avoids disconnecting the chamber from the line 306. The risks of direct contact between the operator and the fluid collected are therefore reduced.

Moreover, the detection and analysis take place on the same perfusion line. Since there is a connection between the chamber 710 and the patient (via the sample collection device 200-400, the channel 300, the container 303 and the line 306), it becomes impossible to make a connection error between the chamber 710 and the flow control means 731; there can be no inversion of reaction chamber 710 between one patient and another patient.

The system according to the invention therefore makes it possible to achieve a closed circuit: the blood is collected, analyzed and compared to that of the transfusion bag and flow permission/prohibition is generated along one and the same loop circuit on the patient.

In the three preceding embodiments, when the analysis is carried out by the analysis means 700-720-721, the latter transmits to the flow control means 730-731 of the second perfusion, the comparison information $I_C$ of the collected body fluid and the sample of given product.

This information is then displayed owing to display means 740-741.

The nursing staff then know if the product of the first perfusion is compatible with the patient and/or the medical situation which has been diagnosed. In the example of blood transfusion, the nursing staff know if the blood of the transfusion bag 800 is of an ABO group compatible with the ABO group of the patient.

In another example, the nursing staff could determine that the antibiotic present in the perfusion bag does not cause an allergic reaction with the patient.

When the comparison information $I_C$ indicates that the product of the first transfusion is compatible with the patient, the nursing staff can act in several ways.

According to a first embodiment, the bag of the first transfusion is not yet in fluid communication with the patient. In this case, as a function of the comparison information $I_C$, the nursing staff put, or do not put, the tubing 102 and the container 103 of the bag 800 into fluid communication.

This embodiment makes it possible to only connect the bag 800 of product of the first perfusion if it is compatible with the patient. This avoids wasting a bag of product since this system makes it possible to recover the bag considered to be incompatible.

According to a second embodiment, the bag 800 is already in fluid communication with the rest of the perfusion circuit.

So that the product does not flow, the flow control means 730, 731 comprises a solenoid valve 751.

The flow control means 730, 731 is arranged in order to block the flow of product of the first perfusion if the comparison information indicates that the body fluid and the product of the first perfusion are incompatible, and to permit the flow of product of the first perfusion if the comparison information indicates that the body fluid and the product of the first perfusion are compatible.

According to a first variant, this solenoid valve 751 can be activated manually by a manual means 900 of flow generation.

Thus, in case of compatibility, the nursing staff activate the manual means 900 of flow generation of said product in the tubing 102. Since the perfusion product is compatible with the patient, the flow control means 730, 731 permits the flow of the product and opens the solenoid valve 751.

If the nursing staff accidentally take the decision to manually generate the flow by activating the generation means 900, when the perfusion product is incompatible with the patient, the flow control means 730, 731 blocks the flow of the product of the first perfusion by keeping the solenoid valve 751 closed.

According to a second variant, the solenoid valve 751 can be activated automatically by the flow control means 730, 731.

It can also be envisaged, for certain applications, for the analysis means to also be able to control the flow control means so that it automatically generates flow of the product of the second perfusion if the body fluid and the product of the second perfusion are compatible, and so that it does not generate flow of the product of the second perfusion if the body fluid and the product of the second perfusion are incompatible.

Thus, in the case of compatibility, the flow control means 730, 731 permits the flow of the product and opens the solenoid valve 751.

On the contrary, in the case of incompatibility, the flow control means 730, 731 blocks the flow of product of the first perfusion by keeping the solenoid valve 751 closed.

The invention therefore allows a final check on the same perfusion line connected to the patient. Therefore, there are no longer risks between the analysis for the final check and the actual implementation of the treatment itself since the check and the treatment authorization are linked directly to the patient, without potentionally erroneous intervention of the nursing staff.

Figure 4:
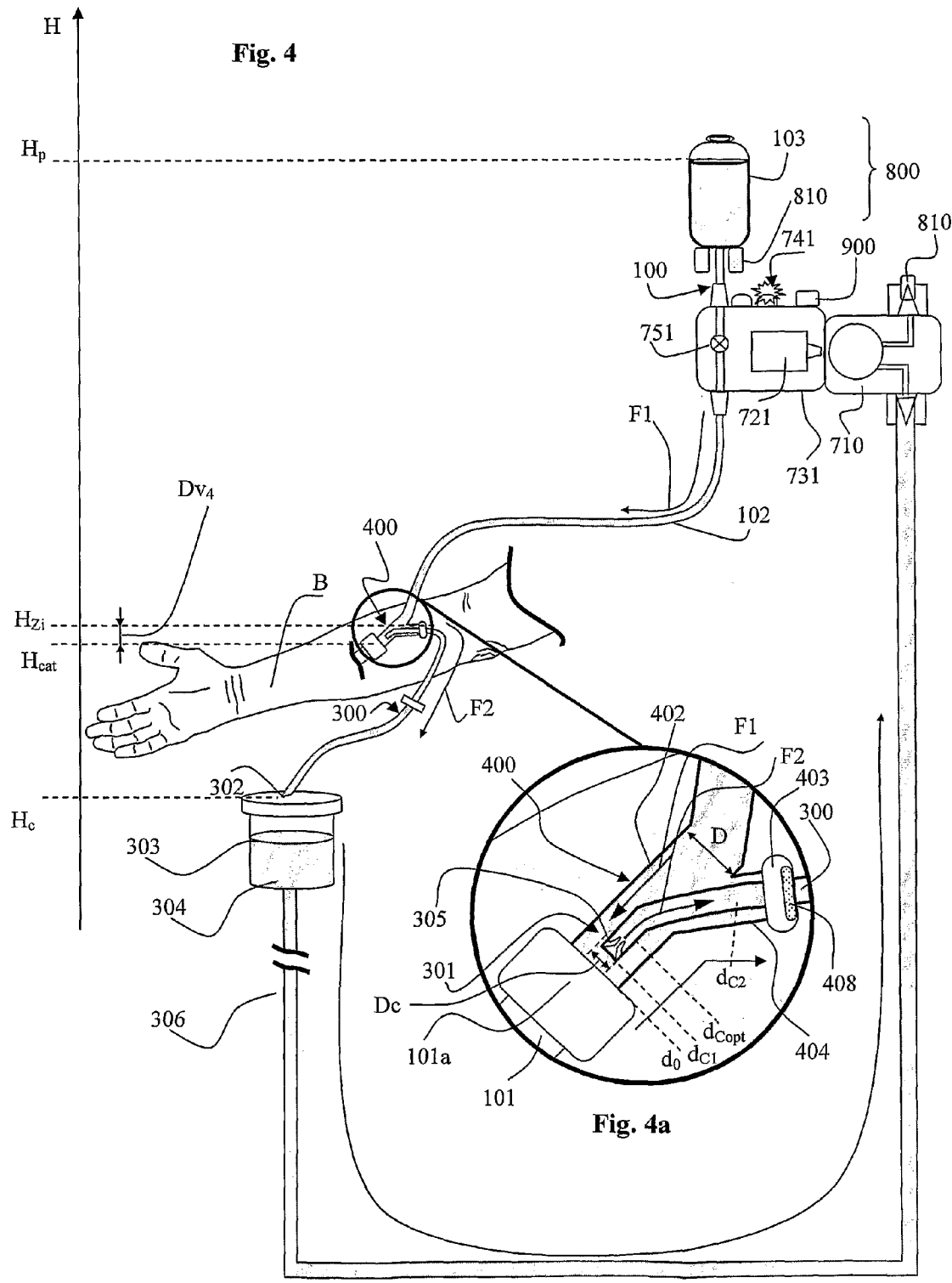
FIG. 4, a schematic plan view of a fourth embodiment of a secure perfusion system according to the invention, comprising a sample collection device that avoids a second needle insertion into the patient.

In order to avoid making two needle insertions in the patient, the invention proposes a system of secure perfusion comprising a sample collection means especially designed to enable, on the one hand, the collection of a sample of body fluid and, on the other hand, the flow of the product of the first perfusion 100. This embodiment is illustrated in FIGS. 4 and 4a.

More specifically, the sample collection means comprises a sample collection channel 300 comprising a proximal end 302 intended to be connected to the sample collection container 303, and a distal end 301.

The sample collection means also comprises a sample collection device 400 intended to be incorporated, not into a patient, but into the fluid circuit of the perfusion 100 previously fitted to a patient, between the catheter and the perfusion container, in an external portion of the fluid circuit relative to the body of the patient.

This device comprises a tubular structure 402 of fluid connection to the fluid circuit of the perfusion 100, equipped with a zone of intubation, in use, of a sample collection channel 300 comprising a distal end 301.

This tubular structure also comprises a holding means 403. This is suitable for enabling, in use, the holding, in the tubular structure, of the portion of the sample collection channel 300 comprising a distal end 301, so that the distal end 301 of the sample collection channel 300 is pointed toward the perfusion catheter 101, in the flow direction F1 of the perfusion product 102, from a container 101 of perfusion product to the perfusion catheter 104.

The term "holding" should be understood in the broad sense. It relates, on the one hand, to a reversible holding of the portion of the sample collection channel inserted in the tubular structure. In this case, the device according to the invention does not comprise a sample collection channel. This must be inserted by the user, during the collection, into the tubular structure (see FIGS. 4 to 11).

The term "holding" also relates to a permanent holding in the tubular structure, of the portion of the sample collection channel so that it only forms one and the same portion comprising two tubes. In this way, in use, a portion of the sample collection channel 2100 is arranged in the tubular structure 2002 so that the distal end 2101 of the sample collection channel 2100 is pointed toward the perfusion catheter 101, in the flow direction F1 of the perfusion product, from a container 103 of perfusion product to the perfusion catheter 101 (see FIG. 12).

In the embodiments of FIGS. 4 to 11, the intubation zone Zi comprises an insertion means.

In the embodiment of FIGS. 4 and 4a, the tubular structure 402 is a Y connection system having a branch intended to be in fluid communication with the tubing 102 of the perfusion 100, and a branch 404 equipped with an intubation zone Zi bearing a holding means 403 and a membrane 408 for the leaktight insertion of the channel 300. This membrane is made of a leaktight material that retains its leaktightness after having been pierced.

Alternatively, the structure of the membrane (thickness and/or stiffness) and its arrangement in the Y system may be such that the sample collection channel is both inserted and held in the usage position, that is to say inside the tubular structure 202. In this case, the membrane carries out the roles of a holding means and an insertion means. In other words, the sample collection channel 300 is inserted and held in the usage position, that is to say inside the tubular structure 202, the distal end 301 of the sample collection channel 300 being pointed toward the perfusion catheter 101, in the flow direction F1 of the perfusion product, from the container 103 of perfusion product to the perfusion catheter 101. Alternatively, the tubular structure may comprise a holding means independent of the membrane which, then, would only be used for the insertion.

The leaktight material that retains its leaktightness after having been pierced is chosen from a silicone polymer, such as polydimethylsiloxane (PDMS), polymethyl methacrylate (PMMA), polyvinyl chloride (PVC) and Tygon® (manufactured by the company Saint-Gobain), etc.

The sample collection channel 300 comprises a distal end 301, which has a stiffness sufficient to pierce the membrane 408, and a proximal end 302 intended to be in fluid communication with a sample collection container 303. The fluid collection container advantageously has a closeable air inlet (not illustrated).

According to one variant that is not illustrated, the holding means is a leaktight connector, for example of Luer lock type. In this case, the channel 300 is equipped with a corresponding Luer lock connector, into which passes, in a leaktight manner, the portion of the channel bearing the distal end 301. The association of the Luer lock connectors enables the insertion of the sample collection channel into the tubular structure and holds the portion of the channel bearing the distal end 301 pointed toward the perfusion catheter 101, in the flow direction F1 of the perfusion product, from a container 103 of perfusion product to the perfusion catheter 101.

In use, the tubular structure 402 is connected to the catheter 101 and the tubing 102. This connection is preferably made using Luer lock connectors. This incorporation takes place in the vicinity of the proximal end 101a of the perfusion catheter 101 and therefore does not take place directly in the patient, but in an external portion of the fluid circuit relative to the body of the patient.

In a second step, via the insertion means 404 of the sample collection device 400, the distal end 301 of the sample collection channel 300 is inserted into the tubular structure 402 of the sample collection device, so that said distal end 301 is pointed toward the perfusion catheter 101, in the flow direction F1 of the perfusion product. The distal end 301 of the sample collection channel 300 remains located outside of the perfusion catheter 101 and, therefore, outside of the patient.

Figure 12:
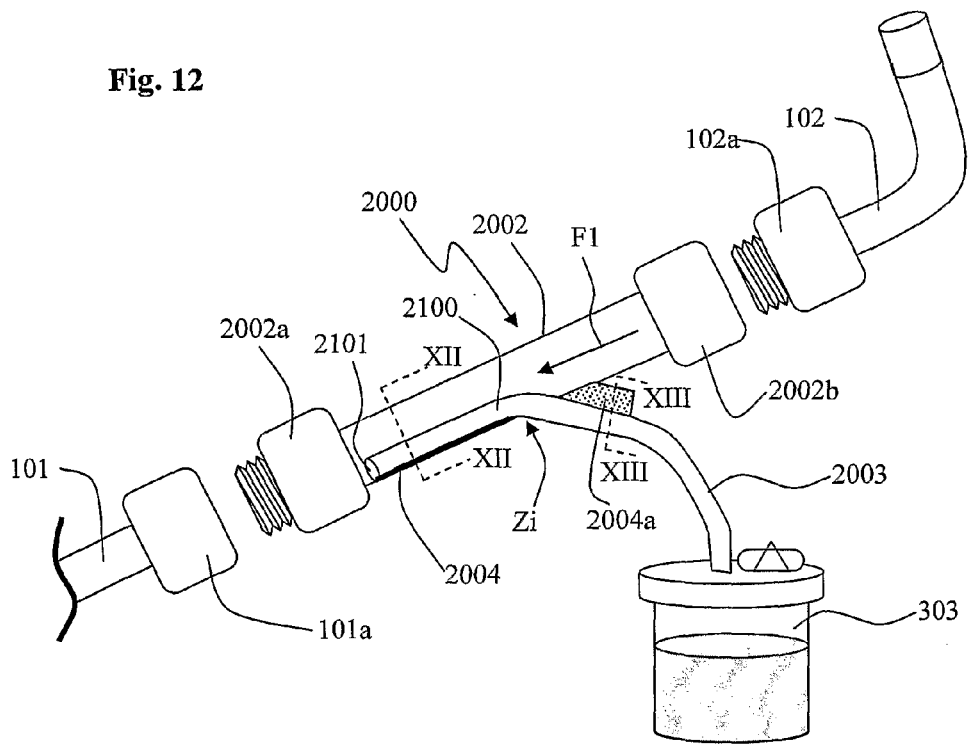
FIG. 12, a schematic plan view of another embodiment of a sample collection device according to the invention, in which the tubular structure includes a portion of the sample collection channel.

Another embodiment of a sample collection device 2000 according to the invention is illustrated in FIG. 12. It comprises a tubular structure 2002 for connection to the fluid circuit of the perfusion represented, in this FIG. 12, by a catheter 101 and tubing 102. For this purpose, the tubular structure 2002, the catheter 101 and the tubing 102 preferably have Luer lock connections, respectively 2002a, 2002b, 101a and 102a.

The sample collection device 2000 also comprises a holding means 2004 suitable for enabling, in use, the holding, inside the tubular structure 2002, of a portion of a sample collection channel 2100 comprising a distal end 2101. In this way, in use, the distal end 2101 of the sample collection channel 2100 is pointed toward the perfusion catheter 101, in the flow direction F1 of the perfusion product.

The portion of the sample collection channel 2100 comprising the distal end 2101 is therefore directly incorporated into the tubular structure 2002, and a portion 2003 of the sample collection channel 2100 comprising a proximal end emerges outside of the tubular structure level with the intubation zone Zi.

The holding means 2004 is here constituted by the mechanical connection between the channel 2100 and the tubular structure. The channel 2100 and the tubular structure 2002 constitute one and the same portion. The holding means may be a longitudinal weld.

The distal end of the sample collection channel is arranged at a given butt-joining distance from the proximal end of the perfusion catheter 101, of between 0 cm and 20 cm, preferably between 0 cm and 3 cm. This distance cannot be adjusted by the nursing staff, but is predefined during the manufacture of the device. This enables easier handling while avoiding an additional technical gesture on the part of the nursing staff.

In FIG. 12, the holding means comprises, optionally, a solid part 2004a resembling the Y branch of the embodiments of FIGS. 4 and 4a. This solid part makes it possible to partially support the portion 2003 emerging from the tubular portion 2002 and, thus, to avoid folding of the channel 2100. This solid part may be located above, below or all around the sample collection channel.

A sample collection device according to the invention that directly incorporates a portion of the sample collection channel prevents the user from having to insert the channel into the tubular structure. Specifically, this insertion is a medical gesture that may not be carried out satisfactorily, for example if the butt-joining distance is too large. Moreover, the insertion may lead to a folding of the channel which prevents the flow of the body fluid to the container 303.

To avoid this folding phenomenon, the sample collection channel 2100 may comprise at least one accordion structure enabling it to bend without forming folds.

This accordion structure may equip the sample collection channel of all the embodiments of the perfusion system according to the invention.

The distal end 301 of the sample collection channel 300 remains located outside of the perfusion catheter and, therefore, outside the body of the patient.

It is therefore an ex vivo installation of the sample collection channel in a fluid circuit of a perfusion located outside of the body of the patient. It is not an in vivo installation, that is to say in the body of the patient.

Next, the perfusion tubing 102 is clamped, then the sample collection channel 300 is unclamped and the sample collection container 303 is brought to a height $H_C$ below the height $H_{cat}$ of the patient's catheter. Advantageously, the sample collection channel and the container are brought to atmospheric pressure owing to the closeable air inlet of the container.

Surprisingly, this enables the blood to flow into the sample collection channel 300, countercurrent along the direction of the arrow F2, relative to the perfusion product which is located between the catheter 101 and the clamp of the tubing 102. The perfusion product located above the sample collection channel and below the clamp of the tubing 102 is not collected at the same time as the blood.

Moreover, it is noticed that it is not necessary to lower the perfusion container 103 in order for the blood to flow into the sample collection channel.

When the blood flows into the sample collection channel 300, the sample collection container 303 is held in this position for a sufficient time to obtain, in the sample collection container 303, the desired sample collection volume 304.

In order to obtain a flow of blood under good conditions (flow rate, comfort of the patient, etc.), the intubation zone Zi of the sample collection device is arranged so that, in the usage position, it is positioned at a given maximum vertical distance $Dv_{max}$ from the proximal end of the catheter 101. The vertical direction is the direction of the gravitational field.

The vertical distance Dv is defined as the distance between the height $H_{Zi}$ of the intubation zone and the height $H_{cat}$ of the perfusion catheter on the height scale H.

The maximum vertical distance $Dv_{max}$ is less than 50 cm. Preferably, it is between −50 and 50 cm (the negative sign means that the intubation zone is below the proximal end of the catheter).

Figure 6:
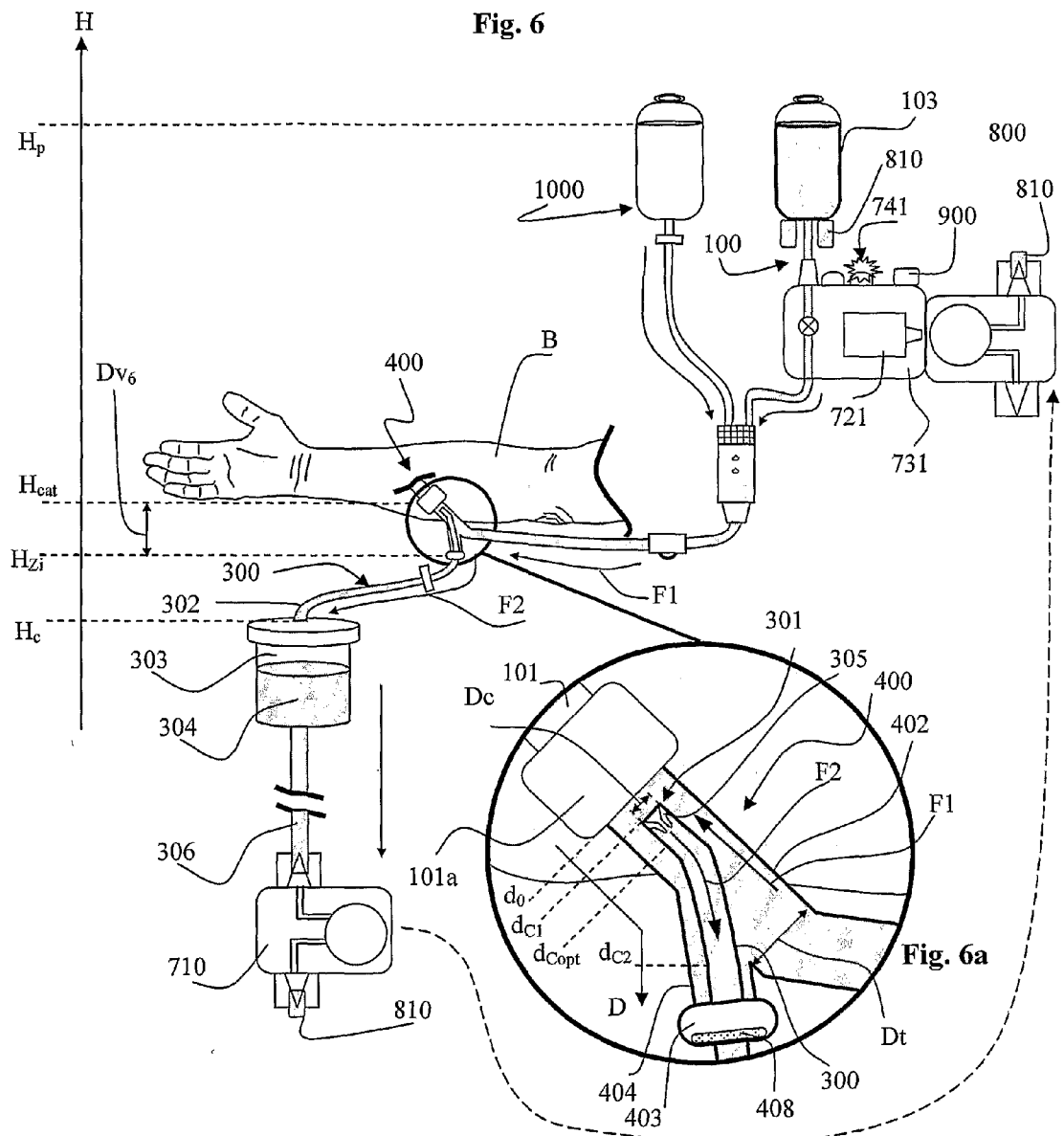
FIG. 6, a schematic plan view of a sixth embodiment of a secure perfusion system according to the invention comprising two perfusions.
Figures 7, 7A:
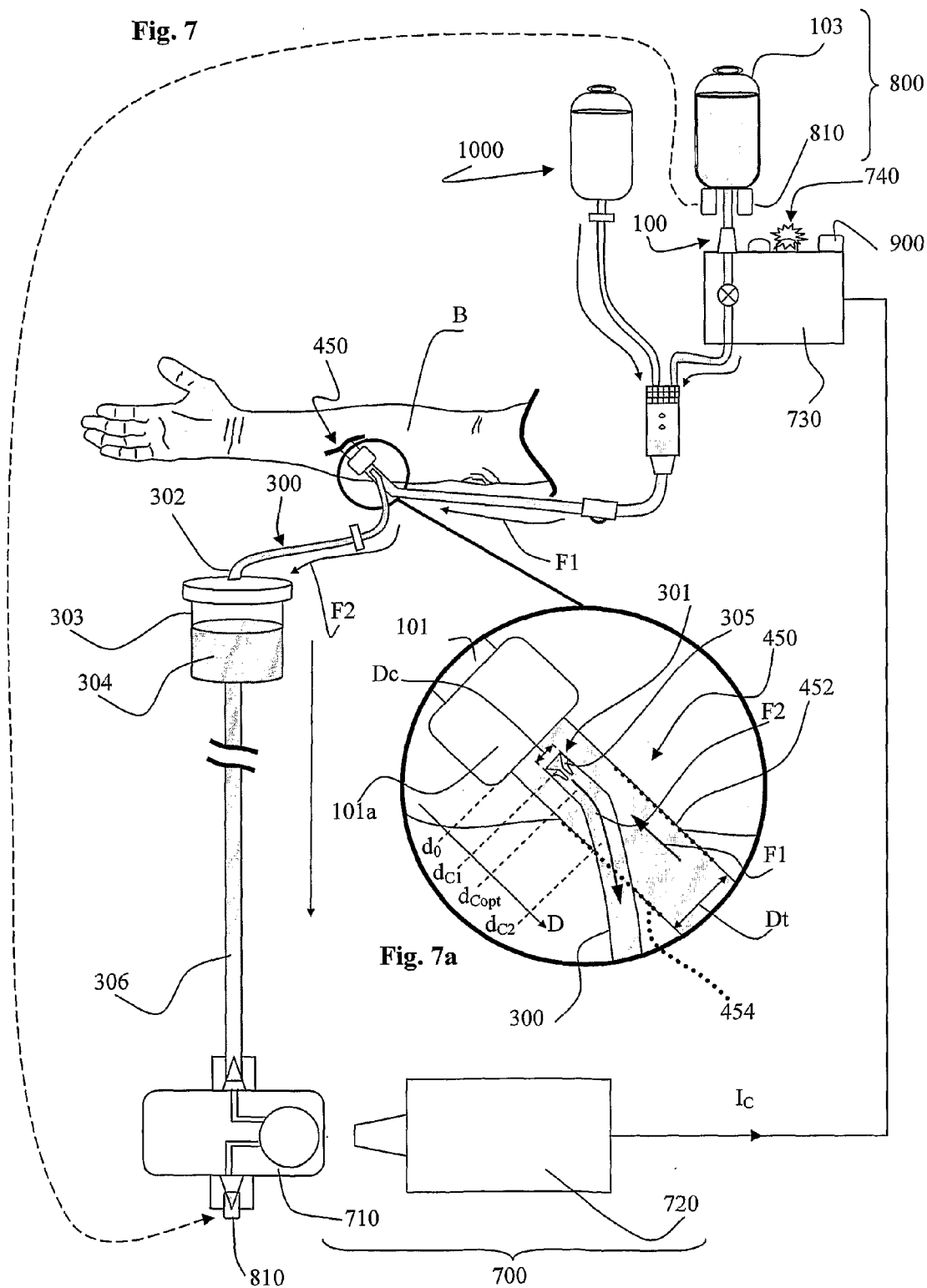
FIG. 7, a schematic plan view of a seventh embodiment of a secure perfusion system according to the invention comprising two perfusions.
FIG. 7*a*, a partial enlargement of FIG. 7 illustrating, in detail, the sample collection device according to the invention.

In FIGS. 6 to 7a, the intubation zone Zi is located below the perfusion catheter 101. The vertical distance, denoted respectively by Dv6 and Dv7, is therefore negative. This arrangement is optimal for obtaining blood flow.

However, in practice, it may happen that the perfusion catheter 101 is located below the intubation zone Zi. This situation, illustrated in FIGS. 4 to 5a, may happen, for example, when the perfusion device according to the invention is positioned in the safety loop. In this case, the vertical distance Dv4-Dv5 is positive.

In order to obtain a flow of blood, the distance Dv4-Dv5 must remain smaller than the given maximum vertical distance $Dv_{max}$.

In practice, and generally, the sample collection device is incorporated into a fluid circuit of the perfusion in the vicinity of the perfusion catheter, that is to say so that the intubation zone is positioned at a distance between 0 and 50 cm, preferably between 5 cm and 15 cm.

In this way, during use, the intubation zone has little risk of being above the proximal end of the catheter, at a vertical distance greater than the given maximum vertical distance $DV_{max}$.

At the very start of the sample collection (transient state), the fluid collected is constituted by a mixture of blood and of perfusion product located between the vascular system of the patient and the distal end 301 of the sample collection channel 300.

It may therefore be preferable to only connect the sample collection container 303 when the blood appears pure (visually, or by any means of analysis).

Alternatively, the volume of perfusion product between the vascular system of the patient and the distal end 301 of the sample collection channel 300 may be known owing to the dimensions of the catheter and to the measurement of the distance $d_{c1}$ referred to as the "butt-joining distance" between the proximal end 101a of the catheter 101 (determining the origin $d_0$ of the distance mark D on FIGS. 4 and 4a) and the distal end 301 of the channel 300. It is therefore possible to calculate the dilution ratio of the blood collected in the container 303.

Figure 13:
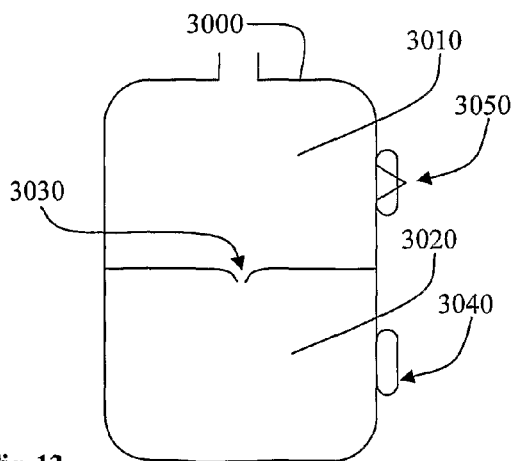
FIGS. 13 and 14, schematic views of two embodiments of a sample collection container according to the invention.
Figure 14:
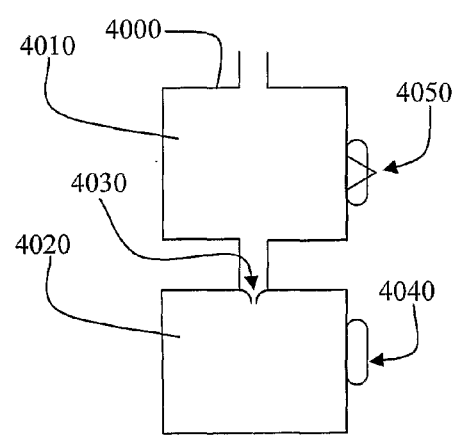

According to another embodiment, a container 3000 may be provided having two compartments 3010 and 3020 separated by a non-return system, such as a valve 3030, a flap, a ball, a float, etc. (see FIG. 13). According to one variant, the two compartments 4010 and 4020 of the container 4000 are mounted independently in series and are separated by a non-return system 4030 (see FIG. 14). In the two examples illustrated, the compartment 3020 or the compartment 4020 furthest downstream must allow the storage of a quantity of body fluid equal to, or slightly greater than, the volume of perfusion product located between the vascular system of the patient and the distal end 301 of the sample collection channel 300. During this storage, the air is evacuated by an air evacuation valve 3040-4040.

When the compartment 3020 or the compartment 4020 furthest downstream is full, the compartment 3010 or the compartment 4010 upstream is filled. The non-return systems 3030-4030 prevent this diluted fluid, located in the compartment furthest downstream, from mixing with the "pure" fluid which is stored in the upstream compartment.

A subsequent analysis could therefore be preferably carried out on the pure fluid. For this purpose, the containers from FIGS. 13 and 14 have a valve 3050-4050 for air evacuation and for connection to a means of analyzing the collected body fluid (not represented in these figures).

Once the body fluid is collected and stored in the container 303, it is analyzed as described previously.

If the body fluid and the perfusion product are compatible, the flow control means 731 permits the flow of the perfusion product into the tubing 102 then into the patient via the catheter 101.

It is not therefore necessary to carry out two needle insertions into the patient for the sample collection and the perfusion.

When a patient is already perfused, for example with a therapeutic fluid, it may be necessary to give the patient a second perfusion of another fluid, such as blood, after the doctor has diagnosed a given medical situation (illness, accident, hemorrhage, etc.).

According to one advantageous embodiment of the invention, the secure perfusion system may be implemented when the patient is already equipped with a first perfusion 1000, without it being necessary to carry out an additional needle insertion into the patient nor any direct surgical intervention on the patient for putting in place the device according to the invention, or for the implementation thereof.

This embodiment is illustrated in FIGS. 5 to 7a. For this purpose, the secure perfusion system according to the invention comprises a sample collection means especially designed to enable, on the one hand, the flow of the products of the first perfusion 1000 and of the second perfusion 100, but also to collect a sample of body fluid.

The first perfusion 1000 comprises a fluid circuit comprising perfusion tubing 1002 and a container 1003 of given perfusion product to be administered to a patient B.

Provided between the tubing 1002 and the container 1003 are preferably a filter 1008, an expansion vessel 1010 and a toothed wheel 1012 for controlling the flow rate of the perfusion product.

The tubing 1002 is connected to the vascular system of the patient by a perfusion catheter 101.

In order to connect the second perfusion 100 to the vascular system of the patient without additional needle insertion, the filter 1008 comprises a means for connection of a second tubing 102.

Alternatively, the tubing 1002 of the first perfusion may comprise a means for connection of the second tubing 102.

A flow control means 731 of the perfusion product is associated with the tubing 102 in order to permit or prohibit the flow of the product of the second perfusion 100.

Figure 5:
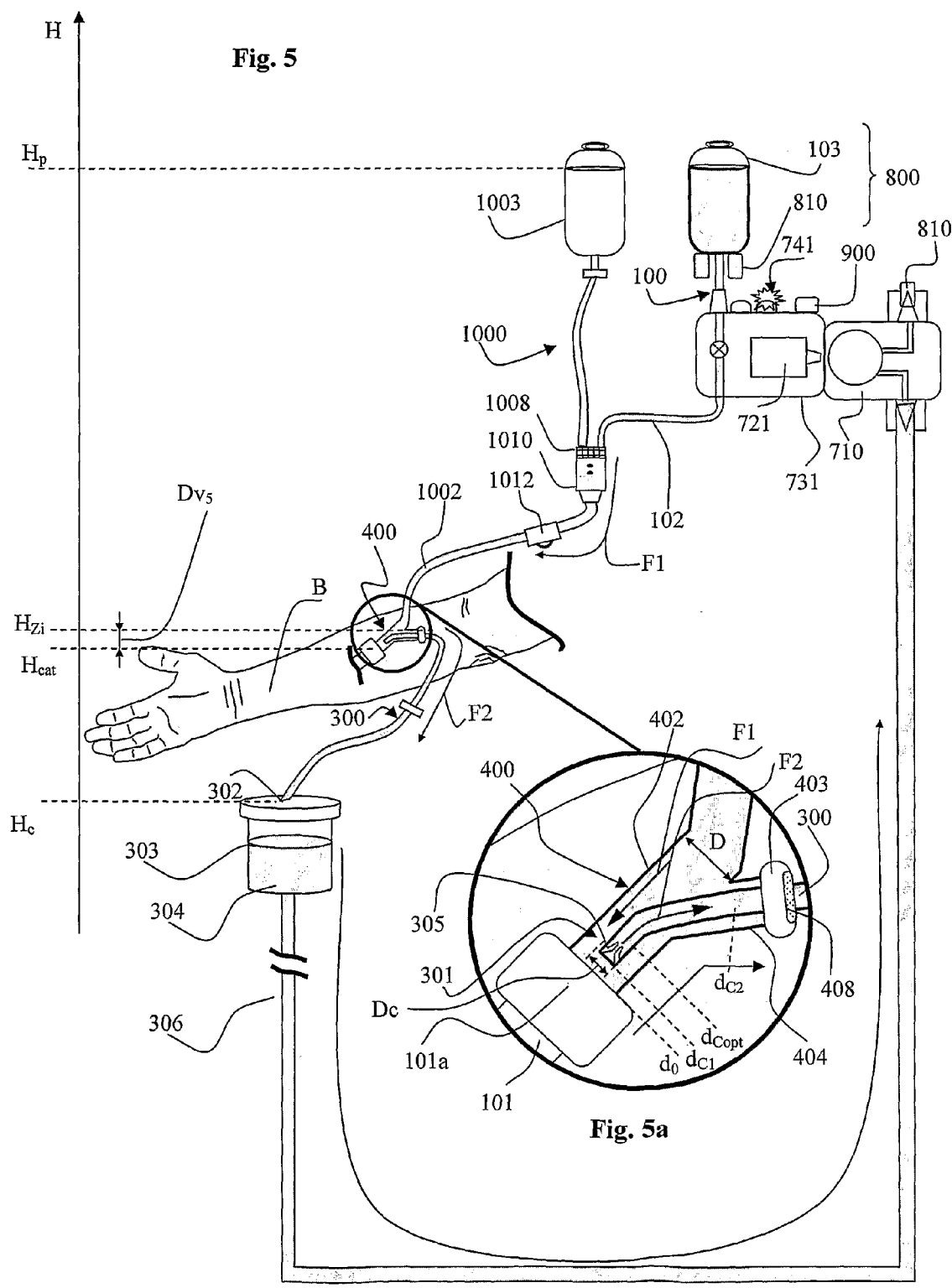
FIG. 5, a schematic plan view of a fifth embodiment of a secure perfusion system according to the invention comprising two perfusions.

As in the embodiment illustrated in FIGS. 4 and 4a, the secure perfusion system according to the invention, illustrated in FIGS. 5 and 5a, comprises a sample collection device 400 intended to be incorporated into the fluid circuit of the first perfusion 1000. This device comprises a tubular structure 402 for fluid connection to the tubing 1002 of the first perfusion 1000, equipped with an intubation zone Zi bearing a holding means 403 and a membrane 408 for the leaktight insertion of the channel 300. The holding means 403 is suitable for enabling, in use, the holding, in the tubular structure 402, of a portion of the sample collection channel 300. The membrane is made of a leaktight material that retains its leaktightness after having been pierced. Alternatively, the structure of the membrane (thickness and/or stiffness) and its arrangement in the Y system may be such that the sample collection channel is both inserted and held in the usage position, that is to say inside the tubular structure 202. In this case, the membrane carries out the roles of a holding means and of an insertion means.

When collection of a sample of body fluid is necessary, here blood, the sample collection device 400 according to the invention is incorporated into the fluid circuit of the first perfusion 1000 previously fitted to a patient B.

This incorporation is carried out in the vicinity of the proximal end 101a of the perfusion catheter 101 and is not therefore carried out directly in the patient, but in an external portion of the fluid circuit relative to the body of the patient.

It is not therefore necessary to carry out an additional needle insertion into the patient. No direct surgical intervention on the patient is necessary for putting into place the device according to the invention, nor for the implementation thereof.

Next, the distal end 301 of the sample collection channel 300 is inserted, via the insertion means 404 of the sample collection device 400, into the tubular structure 402 of the sample collection device, so that said distal end 301 is pointed toward the perfusion catheter 101, in the flow direction F1 of the perfusion product. The distal end 301 of the sample collection channel 300 remains located outside of the perfusion catheter 101 and, therefore, outside of the patient.

This insertion step is unnecessary if a sample collection device that already incorporates a portion of the sample collection channel is used.

Next, the sample collection container 303 is brought to a height $H_c$ below the height $H_{cat}$ of the patient's catheter which enables blood to flow into the sample collection channel, countercurrent along the direction of the arrow F2. The perfusion product located above the sample collection channel and below the clamp of the tubing 102 is not collected at the same time as the blood.

The sample collection takes place in the same way as for the installation illustrated in FIGS. 4 and 4a.

Advantageously, to avoid, for example during poor handling, a return of blood from the sample collection channel toward the fluid circuit of the perfusion, the distal end 301 of the sample collection channel 300 is equipped with a non-return means 305 such as a non-return valve of duckbill or tricuspid type. Alternatively, the non-return means may also be located at the proximal end of the sample collection channel 300.

Next, the implementation of the secure perfusion system is similar to that described in FIGS. 1 to 3 and enables the same advantages.

Thus, with the embodiment illustrated in FIGS. 4 to 5a, the sample collection container 303 is in fluid communication, via a line 306, with the reaction chamber 710.

The line 306 is long enough to enable an operator, when the reaction chamber is ready for the analysis and the comparison, to place the chamber 710 on a means (not represented) for attachment to a flow control means 731. The latter is equipped with a means 721 of detection and analysis and a means 741 for displaying the comparison information $I_C$ (not represented) transmitted by the means 721.

The attachment means may be a clamp sandwiching the reaction chamber 710, so that the position of the chamber is optimal for the detection and analysis by the means 721.

This embodiment avoids disconnecting the chamber from the line 306. The risks of direct contact between the operator and the fluid collected are therefore reduced.

Similarly, with the embodiment illustrated in FIGS. 6 and 6a, the reaction chamber 710 is, as in FIG. 2, connected to the container 303 of collected fluid and to a sample 810 of given product.

When the reaction chamber is ready for the analysis and the comparison, the operator disconnects it from the line 306 (a closure valve, not represented, is preferably provided for this purpose) and connects it to a flow control means 731. The latter is equipped with a means 721 of detection and analysis and a means 741 for displaying the comparison information $I_C$ (not represented) emitted by the means 721. The connection of the chamber 710 to the control means 731 may be made using an attachment means (not represented).

Finally, with the embodiment illustrated in FIGS. 7 and 7a, the detection means 720 of the analysis means 700, located in the vicinity of the reaction chamber 710, transmits comparison information $I_C$ to a flow control means 730 of the first perfusion. The flow control means 730 is preferably equipped with a means 740 for displaying the comparison information.

Practically, the analysis means 700 is, in this embodiment, located below the patient's catheter, in the vicinity of the sample collection container 303.

Such an embodiment has the advantage of only requiring a short length of fluid lines (channel 300 and line 306). However, the overall space requirement of the system may be large since it comprises an analysis means 700 and an independent flow control means 730.

FIGS. 7 and 7a also illustrate another embodiment of a sample collection device 450 according to the invention.

In these figures, the fluid sample collection device 450 according to the invention comprises a tubular structure 452 for connection to the fluid circuit of the perfusion 1000 equipped with an intubation zone Zi comprising a means 454 for insertion, into the tubular structure 452, of a portion of a sample collection channel 300.

In this embodiment, the insertion means 454 is a membrane made of a leaktight material that retains its leaktightness after having been pierced. This membrane 454 may occupy all or part of the wall of the tubular structure 452. This membrane 454 has a structure (thickness and/or stiffness and/or material and/or arrangement) that enables it to carry out both the role of holding means and the role of insertion means. In other words, the sample collection channel 300 is inserted and held in the usage position, that is to say inside the tubular structure 452, the distal end 301 of the sample collection channel 300 being pointed toward the perfusion catheter 101, in the flow direction F1 of the perfusion product, from the container 1003 of perfusion product to the perfusion catheter 101. Alternatively, the tubular structure may comprise a holding means independent of the membrane which then would only be used for the insertion.

The sample collection device according to the invention may be incorporated into the fluid circuit of the perfusion between the perfusion catheter and the perfusion tubing. For this, the sample collection device comprises:

a means for connection to a proximal end of the perfusion catheter, and a means for connection to the distal end of the perfusion tubing.

In order to install this device, the operator disconnects the proximal end of the perfusion catheter and the distal end of the perfusion tubing, and connects the device.

The connection means may be of Luer lock type.

This embodiment nevertheless involves temporarily disconnecting the perfusion.

It may be preferable to provide a catheter or perfusion tubing that is pre-equipped, during its manufacture, with a sample collection device according to the invention.

As shown in FIGS. 8 and 9, a perfusion catheter 500 according to the invention comprises:

a distal end 502 intended to be inserted into a patient;

a proximal end 504 intended to be connected, for example via a Luer lock connector 505, with a distal end of a perfusion tubing; and between the distal end 502 and the proximal end 504, a device 506-509 for collecting a sample of body fluid according to the invention, arranged so that, in use, the intubation zone Zi is positioned at a given maximum vertical distance $Dv_{max}$ from the proximal end of the catheter.

This arrangement enables a good flow of the body fluid during use. The given maximum vertical distance $Dv_{max}$ is between 0 cm and 50 cm.

In these figures, the needle for perforating the catheter has not been represented.

In the embodiment of FIG. 8, the device 506 has a tubular structure 507 which is a Y connection system comprising a holding means 503 equipped with an insertion membrane 508 made of a leaktight material that retains its leaktightness after having been pierced. This tubular structure is similar to that which was described in connection with FIGS. 4 to 6a.

In the embodiment of FIG. 9, the device 509 has a tubular structure 501 equipped with a membrane 510 made of a leaktight material that retains its leaktightness after having been pierced. This membrane 510 has a structure (thickness and/or stiffness and/or material and/or arrangement) that enables it to carry out both the role of holding means and the role of insertion means. This membrane 510 is similar to that which was described in connection with FIGS. 7 and 7a.

Thus, when the perfusion is put in place with this catheter according to the invention, the sample collection device according to the invention is incorporated into the fluid circuit of the perfusion between the perfusion catheter and the perfusion tubing.

Similarly, as shown in FIGS. 10 and 11, a perfusion tubing 600 according to the invention comprises:

a proximal end 602 intended to be connected to a container of a first perfusion product;

a distal end 604 intended to be connected, for example via a Luer lock connector 605, with a proximal end of a perfusion catheter inserted into a patient; and between the proximal end 602 and the distal end 604, a device 606-609 for collecting a sample of body fluid according to the invention, arranged so that, in use, the intubation zone is positioned at a given maximum vertical distance $Dv_{max}$ from the proximal end of the perfusion catheter.

This sample collection device is, preferably, arranged as close as possible to the distal end 604, so that, in the usage position, the intubation zone is positioned at a distance between 0 cm and 50 cm, preferably between 5 and 15 cm.

In the embodiment of FIG. 10, the device 606 has a tubular structure 607 which is a Y connection system comprising a holding means 603 equipped with an insertion membrane 608 made of a leaktight material that retains its leaktightness after having been pierced. This tubular structure is similar to that which was described in connection with FIGS. 4 to 6a.

In the embodiment of FIG. 11, the device 609 has a tubular structure 601 equipped with a membrane 610 made of a leaktight material that retains its leaktightness after having been pierced. This membrane 610 has a structure (thickness and/or stiffness and/or material and/or arrangement) that enables it to carry out both the role of holding means and the role of insertion means. This membrane 610 is similar to that which was described in connection with FIGS. 7 and 7a.

Thus, when the perfusion is put in place, with this tubing according to the invention, the sample collection device according to the invention is incorporated into the fluid circuit of the perfusion between the perfusion catheter and the perfusion tubing.

With a catheter or tubing integrating, from manufacture onwards, a sample collection device according to the invention, it is not necessary to temporarily stop the perfusion in order to incorporate the sample collection device according to the invention.

In all the secure perfusion systems set out in FIGS. 4 to 11, the ratio between the diameter Dc of the sample collection channel and the diameter Dt of the tubular structure of the sample collection device is, preferably, less than 1, and typically between ½₀ and ⅓. This makes it possible to ensure the continuity of the supply of perfusion product in spite of the blood sample collection.

Similarly, the external diameter of the perfusion catheter is, preferably, between 14 G (gauge) and 24 G, advantageously between 14 G and 18 G.

The larger this diameter, the greater the sample collection flow rate may be. By playing with the height of the container relative to the patient's catheter, it is possible to adjust the flow rate and increase the throughput. The sample collection can therefore be carried out in a time that is comfortable for the patient, of ten seconds or less.

Preferably, the sample collection channel has a length between its two ends of between 10 cm and 100 cm, advantageously between 20 cm and 50 cm.

According to another embodiment that is not illustrated, the sample collection device comprises a container, advantageously equipped with a closeable air inlet, connected to tubing that can be connected at its distal end via a connection of Luer lock type. This system may be put in place on a three-way stopcock that is already in place, positioned on an extension or on a stopcock ramp connected on the one hand to the catheter in place on the patient and on the other hand to the perfusion tubing. The sample collection is then carried out by lowering the container, as described previously. This embodiment has the advantage of being very simple. Nevertheless, it leads to a diluted volume (blood and perfusion fluid) and to a filling time that are greater than with the embodiments described previously.

The object of the process according to the invention is not to diagnose the medical situation (illness, accident, hemorrhage, etc.) and/or to choose the treatment ad hoc since these steps have previously been carried out by the doctor, depending on the medical situation and the patient.

The process aims to ensure that the treatment which will be given is indeed in accordance with the choice of the doctor. For example, the doctor has diagnosed the medical situation X and he/she has chosen to treat the patient Y with the product Z which is compatible with the medical situation X and the patient Y. After this diagnosis, the process according to the invention makes it possible to carry out a final check during the implementation of the treatment, by verifying that it is indeed the product Z, compatible with the medical situation X and the patient Y, which is applied.

For the example of blood, the process according to the invention makes it possible to carry out a final check during the implementation of the transfusion, by verifying that the blood of the transfusion bag, needed for the treatment of the medical situation X previously diagnosed, is compatible with the ABO group of the blood of patient Y.

This process does not therefore aim to diagnose a medical situation requiring a blood transfusion or to prevent a medical situation requiring a blood transfusion.

It is a method that aims to avoid a medical accident (incompatibility between the treatment product and the patient) and not one that aims to treat a pathological condition.

The invention claimed is:

1. A system for the secure perfusion of a body fluid, comprising:
    a fluid circuit comprising a perfusion catheter, perfusion tubing and a container of given perfusion product to be perfused to a patient;
    a sample collection channel comprising a proximal end and a distal end;
    a sample collection device configured to be incorporated into the fluid circuit, the sample collection device comprising a tubular structure for connection to the fluid circuit,
        the tubular structure comprising a zone of intubation and a holding member, wherein said holding member holds the distal end of the sample collection channel within the zone of intubation of the tubular structure, such that said distal end of the sample collection channel is pointed toward the perfusion catheter, in the flow direction of the perfusion product, from the container of perfusion product to the perfusion catheter,
    a sample collection container configured to be connected to, and in fluid communication with the proximal end of the sample collection channel
    a means configured for analyzing and comparing the collected body fluid and a sample of given product;
    a means configured for fluid connection between the means configured for analyzing and the sample collection container;
    a means configured for controlling the flow of the perfusion product in the tubing, the means configured for analyzing being configured to transmit to the means configured for controlling the flow, a comparison information of the collected body fluid and the sample of given product.

2. The secure perfusion system as claimed in claim 1, wherein the means configured for analyzing and comparing is configured to control the means configured for controlling the flow in order to block the flow of the perfusion product if the comparison information indicates that the body fluid and the perfusion product are incompatible, and in order to permit the flow of the perfusion product if the comparison information indicates that the body fluid and the perfusion product are compatible.

3. The secure perfusion system as claimed in claim 1, comprising a display device for displaying the comparison information of the body fluid collected and the sample of given product.

4. The secure perfusion system as claimed in claim 1, wherein the means configured for analyzing is configured to control the means configured for controlling the flow in order to automatically generate the flow of the perfusion product if the body fluid and the perfusion product are compatible, and in order to not generate the flow of the perfusion product if the body fluid and the perfusion product are incompatible.

5. The secure perfusion system as claimed in claim 1, wherein the means configured for analyzing comprises a reaction chamber and means configured for detecting.

6. The secure perfusion system as claimed in claim 1, wherein the intubation zone is arranged to be positioned at a given maximum vertical distance ($Dv_{max}$) from the proximal end of the catheter.

7. The secure perfusion system as claimed in claim 6, wherein the given maximum vertical distance ($Dv_{max}$) is between 0 cm and 50 cm.

8. The secure perfusion system as claimed in claim 1, wherein a portion comprising the distal end of the sample collection channel is fixed in the tubular structure, and a portion comprising the proximal end of the sample collection channel emerges outside of the tubular structure level with the intubation zone.

9. The secure perfusion system as claimed in claim 1, wherein the intubation zone comprises a means configured for inserting, said means for inserting being suitable for enabling the insertion of the portion of the sample collection channel comprising the distal end, into the tubular structure.

10. The secure perfusion system as claimed in claim 9, wherein the means configured for inserting is chosen from:
    a leaktight material remaining leaktight after having been pierced; and
    a leaktight connector.

11. The secure perfusion system as claimed in claim 10, wherein said leaktight material is chosen from a silicone polymer selected from the group consisting of polydimethylsiloxane (PDMS), polymethyl methacrylate (PMMA), and polyvinyl chloride (PVC).

12. The secure perfusion system as claimed in claim 1, wherein the sample collection device additionally comprises:
    a means configured for connecting to a proximal end of the perfusion catheter, and
    a means configured for connecting to a distal end of the perfusion tubing.

13. The secure perfusion system as claimed in claim 1, wherein the sample collection channel has a length, between the proximal and distal ends, of between 10 cm and 100 cm.

14. The secure perfusion system as claimed in claim 1, equipped with a perfusion catheter comprising:
    a distal end configured to be inserted into a patient;
    a proximal end configured to be connected with a distal end of the perfusion tubing;
    the sample collection device arranged between the distal end and the proximal end, and comprising a tubular structure for connection to the fluid circuit, equipped:
        with the zone of intubation of a sample collection channel comprising a distal end; and
        with a means configured for holding, in the tubular structure, the portion of the sample collection channel comprising a distal end, so that, in use, said distal end is pointed toward the perfusion catheter, in the flow direction of the perfusion product, from a container of perfusion product to the perfusion catheter.

15. The secure perfusion system as claimed in claim 1, comprising perfusion tubing comprising:
    a proximal end configured to be connected to a container of a perfusion product;
    a distal end configured to be connected with a proximal end of a perfusion catheter inserted into a patient;
    the sample collection device arranged between the distal end and the proximal end, and comprising a tubular structure for connection to the fluid circuit, equipped:
        with the zone of intubation of a sample collection channel comprising a distal end; and
        with a means configured for holding in the tubular structure, the portion of the sample collection channel comprising a distal end, so that, in use, said distal end is pointed toward the perfusion catheter, in the flow direction of the perfusion product, from a container of perfusion product to the perfusion catheter.

16. The secure perfusion system as claimed in claim 14, wherein the intubation zone is positioned at a given maximum vertical distance ($Dv_{max}$) from the proximal end of the catheter.

17. The secure perfusion system as claimed in claim 16, wherein the given maximum vertical distance ($Dv_{max}$) is between 0 cm and 50 cm.

18. A process for implementing a secure perfusion system as claimed in claim 1, the sample collection device of which has been previously fitted to a patient, characterized in that it comprises the following steps:
    placing the sample collection device, the sample collection container and the means for analyzing and comparing in fluid communication;
    bringing the sample collection container to a height below that of the catheter of the patient, so that the body fluid flows into the sample collection channel, toward the sample collection container;
    holding the sample collection container at a height below that of the catheter of the patient for a sufficient time to obtain, in the sample collection container, a volume sufficient to constitute a collection of a sample of body fluid;
    analyzing and comparing the collected body fluid and the sample of given product;
    generating comparison information of the collected body fluid and the sample of given product;
    transmitting the comparison information to a means for controlling the flow of the perfusion product;
    blocking the flow of the perfusion product if the comparison information indicates that the body fluid and the perfusion product are incompatible, and permitting the flow of the perfusion product if the comparison information indicates that the body fluid and the perfusion product are compatible.

19. The process as claimed in claim 18, comprising, in addition, a step of displaying the comparison information of the collected body fluid and the sample of given product.

20. A process for implementing a secure perfusion system as claimed in claim 1, characterized in that it comprises the following steps:

incorporating the sample collection device into a fluid circuit of a first perfusion previously fitted to a patient equipped with a perfusion catheter, in an outer portion of the fluid circuit relative to the body of the patient;

holding, inside the tubular structure, the portion of the sample collection channel comprising the distal end, so that said distal end is pointed toward the perfusion catheter, in the flow direction of the perfusion product, from a container of perfusion product to the perfusion catheter;

placing the sample collection channel, the sample collection container and the means for analyzing and comparing in fluid communication;

bringing the sample collection container to a height below that of the catheter of the patient, so that the body fluid flows into the sample collection channel, countercurrent compared to the perfusion products, then toward the sample collection container;

holding the sample collection container at a height below that of the catheter of the patient for a sufficient time to obtain, in the sample collection container, a volume sufficient to constitute a collection of a sample of body fluid;

analyzing and comparing the collected body fluid and a sample of given product;

generating comparison information of the collected body fluid and the sample of given product;

transmitting the comparison information to a means for controlling the flow of the product of a second perfusion;

blocking the flow of the product of the second perfusion if the comparison information indicates that the body fluid and the product of the second perfusion are incompatible, and permitting the flow of the product of the second perfusion if the comparison information indicates that the body fluid and the product of the second perfusion are compatible.

21. The process as claimed in claim 20, wherein the sample collection device is arranged so that, in use, the intubation zone is positioned at a given maximum vertical distance ($Dv_{max}$) from the proximal end of the catheter.

22. The process as claimed in claim 21, wherein the given maximum vertical distance ($Dv_{max}$) is between 0 cm and 50 cm.

23. The process as claimed in claim 20, wherein the distal end of the collection channel is arranged at a given distance from a proximal end of the perfusion catheter, said distance being referred to as the "butt-joining distance" and between 0 cm and 20 cm.

* * * * *